(12) United States Patent
Olsen et al.

(10) Patent No.: US 7,307,087 B2
(45) Date of Patent: Dec. 11, 2007

(54) TREATMENT OF AFFECTIVE DISORDERS BY THE COMBINED ACTION OF A NICOTINIC RECEPTOR AGONIST AND A MONOAMINERGIC SUBSTANCE

(75) Inventors: Gunnar M. Olsen, Frederiksberg (DK); Dan Peters, Malmö (SE); Elsebet Østergaard Nielsen, København K (DK)

(73) Assignee: Neurosearch A/S, Ballerup (DK)

( * ) Notice: Subject to any disclaimer, the term of this patent is extended or adjusted under 35 U.S.C. 154(b) by 365 days.

(21) Appl. No.: 10/380,653

(22) PCT Filed: Oct. 10, 2001

(86) PCT No.: PCT/DK01/00661

§ 371 (c)(1),
(2), (4) Date: Mar. 17, 2003

(87) PCT Pub. No.: WO02/30405

PCT Pub. Date: Apr. 18, 2002

(65) Prior Publication Data

US 2004/0092508 A1  May 13, 2004

(30) Foreign Application Priority Data

Oct. 13, 2000  (DK) .............................. 2000 01535

(51) Int. Cl.
*A61K 31/44* (2006.01)
*C07D 451/02* (2006.01)
*C07D 401/00* (2006.01)
*C07D 405/00* (2006.01)

(52) U.S. Cl. .................. 514/304; 546/124; 546/125; 546/126

(58) Field of Classification Search ........ 546/124–126; 514/304
See application file for complete search history.

(56) References Cited

U.S. PATENT DOCUMENTS 6,100,275 A * 8/2000 Moldt et al. ................. 514/304
6,645,977 B1 * 11/2003 Peters et al. ................. 514/304
6,680,328 B2 * 1/2004 Peters et al. ................. 514/304

FOREIGN PATENT DOCUMENTS

| WO | WO 96/33710 A1 | 10/1996 |
| WO | WO 97/13770 A1 | 4/1997 |
| WO | WO 98/54181 A1 | 12/1998 |
| WO | WO 98/54182 A1 | 12/1998 |
| WO | WO 99/21834 A1 | 5/1999 |
| WO | WO 99/38866 A1 | 8/1999 |
| WO | WO-99/65492 A1 | 12/1999 |
| WO | WO 00/15217 A1 | 3/2000 |
| WO | WO 00/15218 A1 | 3/2000 |
| WO | WO 00/15219 A1 | 3/2000 |
| WO | WO 00/25783 A1 | 5/2000 |
| WO | WO 00/32600 A1 | 6/2000 |
| WO | WO 00/44746 A1 | 8/2000 |
| WO | WO 00/45846 A1 | 8/2000 |
| WO | WO 00/64885 A1 | 11/2000 |

OTHER PUBLICATIONS

Hennings et al. PubMed ID:9221950, 1997.*
Harrison's Principles of Internal Medicine, 13th ed., 1994, p. 2400-2409, McGraw-Hill.*
Merck Manual, 16th ed., 1992, p. 1592-1614.*
Qian Li, et al. The Journal of Pharmacology and Experimental Therapeutics, vol. 266, No. 2, pp. 836-844, 1993.
Berendsen H. H. G , et al. European Journal of Pharmacology, vol. 253, pp. 83-89, 1994.

* cited by examiner

*Primary Examiner*—San-Ming Hui
(74) *Attorney, Agent, or Firm*—Birch, Stewart, Kolasch & Birch, LLP

(57) ABSTRACT

This invention relates to use of the combined action of a nicotinic acetylcholine receptor agonist and a monoaminergic substance for the treatment of affective disorders, as well as to pharmaceutical compositions comprising these substances and chemical substances for use according to the invention.

7 Claims, No Drawings

TREATMENT OF AFFECTIVE DISORDERS BY THE COMBINED ACTION OF A NICOTINIC RECEPTOR AGONIST AND A MONOAMINERGIC SUBSTANCE

This application is the national phase under 35 U.S.C. § 371 of PCT International Application No. PCT/DK01/00661 which has an International filing date of Oct. 10, 2001, which designated the United States of America.

TECHNICAL FIELD

This invention relates to use of the combined action of a nicotinic acetylcholine receptor agonist and a monoaminergic substance for the treatment of affective disorders, as well as to pharmaceutical compositions comprising these substances and chemical substances for use according to the invention.

BACKGROUND ART

Selective monoamine reuptake inhibitors, and in particular serotonin reuptake inhibitors (SSRI's), are the gold standard for treating depression. However, their most severe drawback is that while the side effects set in almost immediately, no substantial antidepressant effect will be seen within the first 2 to 4 weeks, leaving a window of vulnerability during which the patent might be non-compliant with therapy. While co-administration of fast-acting antidepressants may overcome this, it is more preferable to counteract the self-inhibitory mechanism that delays onset of SSRI effects.

There are good indications that this may be achieved by blocking certain receptors that down-regulate the discharge of serotonin as the concentration of neurotransmitter in the synaptic cleft rises. Thus WO 96/33710 (Astra) describes a combination of a 5-HT uptake inhibitor with a selective 5-$HT_{1A}$ antagonist, and WO 00/15217 (AstraZeneca), WO 00/15218 (AstraZeneca) and WO 00/15219 (AstraZeneca) disclose specific examples of such combinations.

Another combination involving nicotinic ligands, however for a quite different use, is disclosed in WO 00/45846 (Synthelabo). This patent publication describes the use of nicotine or a nicotinic ligand in combination with a monoamine oxidase (MAO) inhibitor for the treatment of tobacco withdrawal symptoms, which combination shows reduced cardiovascular side effects.

Finally WO 00/25783 (Carlsson & Carlsson) describes the use of a nicotinic receptor agonist in the treatment of obsessive compulsive disorder (OCD). A combination therapy and the treatment of other affective disorders are not described.

SUMMARY OF THE INVENTION

According to the invention it has now been found that the action of a nicotinic acetylcholine receptor agonist potentiate the monoaminergic action, so the combination of a nicotinic acetylcholine receptor agonist and a monoamine agonist or antagonist or a monoamine reuptake inhibitor for use in the treatment of affective disorders may result in a faster onset of action and an increased success rate. The invention therefore resides in the combined action of a nicotinic acetylcholine receptor agonist and a monoamine agonist or antagonist or a monoamine reuptake inhibitor, or the dual action of a substance possessing both nicotinic acetylcholine receptor agonist activity and monoamine agonist or antagonist activity or monoamine reuptake inhibiting activity, for the treatment of affective disorders.

Accordingly, in its first aspect, the invention provides a method of treatment, prevention or alleviation of an affective disorder, disease or condition in a subject, which method comprises administering to said subject a therapeutically effective amount of one or more compounds having nicotinic acetylcholine agonistic activity and monoamine agonistic or antagonistic or reuptake inhibiting activity.

In another aspect the invention provides a pharmaceutical composition comprising a therapeutically effective amount of a nicotinic acetylcholine agonist and a monoamine reuptake inhibitor, together with at least one pharmaceutically acceptable carrier or diluent.

In a third aspect the invention relates to the use of a nicotinic acetylcholine agonist and a monoamine reuptake inhibitor for the manufacture of a medicament for the treatment, prevention or alleviation of an affective disorder, disease or condition in a subject.

In quite another aspect the invention provides nicotinic acetylcholine agonist represented by Formula I

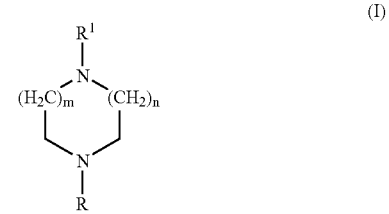

(I)

wherein
n is 1, 2 or 3; and
m is 0, 1 or 2; and
R represents hydrogen, alkyl, cycloalkyl, cycloalkylalkyl, alkoxy, acyl or benzyl; and
$R^1$ represents 5-bromo-3-pyridyl; 5-bromo-3-pyridyl; 6-chloro-3-pyridyl; 6-bromo-5-methoxy-3-pyridyl; 6-bromo-3-pyridyl; 6-bromo-5-chloro-3-pyridyl; 5,6-dibromo-3-pyridyl; 6-chloro-5-bromo-3-pyridyl; 6-iodo-5-methoxy-3-pyridyl; 5,6-dichloro-3-pyridyl; 5-bromo-6-chloro-2-pyrazinyl; 6-bromo-5-etynyl-3-pyridyl; 6-chloro-5-methoxy-3-pyridyl; 6-phenyl-3-pyridazinyl; 6-chloro-2-pyrazinyl; 6-chloro-3-pyridazinyl; 6-iodo-3-pyridazinyl; 6-(1-benzimidazolyl)-3-pyridazinyl; 2-pyrazinyl; 6-chloro-2-pyrazinyl; 6-phenyl-3-pyridyl; 5-chloro-6-phenyl-3-pyridyl; 5-chloro-6-methyl-3-pyridyl; 5-etynyl-3-pyridyl; 5-bromo-3-pyridyl; 5-methoxy-6-bromo-3-pyridyl; 6-bromo-3-pyridyl; 5-chloro-6-bromo-3-pyridyl; 5,6-dibromo-3-pyridyl; 5-bromo-6-chloro-3-pyridyl; 5-methoxy-6-iodo-3-pyridyl; or 5,6-dichloro-3-pyridyl.

In still another aspect the invention provides 8-azabicyclo [3.2.1]oct-2-ene derivatives represented by Formula VI,

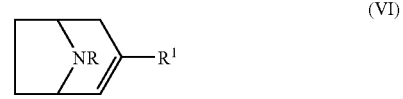

(VI)

any of its enantiomers or any mixture of its enantiomers, or a pharmaceutically acceptable salt thereof;
wherein
R is hydrogen, alkyl, alkenyl, cycloalkyl, cyanoalkyl, phenyl, naphthyl or benzyl; and $R^1$ is

wherein $R^2$ is hydrogen, alkyl, cycloalkyl, or amino; or furanyl, thienyl, pyrrolyl, oxazolyl, isoaxzolyl, imidazolyl, pyridyl, pyrimidinyl or thiazolyl, which heteroaryl group is optionally substituted one or more times with substituents selected from the group consisting of alkyl, cycloalkyl, alkoxy, cyanoalkyl, halogen, $CF_3$, $OCF_3$, CN, amino, nitro, and furyl; or naphthyl, indolyl, benzofuranyl, benzothienyl, benzimidazolyl, benzothiazolyl, quinolinyl, isoquinolinyl or thienothienyl, which bicyclic group is optionally substituted one or more times with substituents selected from the group consisting of alkyl, cycloalkyl, alkoxy, cyanoalkyl, halogen, $CF_3$, $OCF_3$, CN, amino, nitro and furyl.

Other objects of the invention will be apparent to the person skilled in the art from the following detailed description and examples.

DETAILED DISCLOSURE OF THE INVENTION

In its first aspect the present invention provides a method for treatment, prevention or alleviation of an affective disorder, disease or condition in a subject, which method comprises administering to said subject a therapeutically effective amount of one or more compounds having nicotinic acetylcholine agonistic activity and monoamine agonistic or antagonistic or reuptake inhibiting activity.

The subject to be treated according to this invention is a living body, preferably a mammal, most preferably a human, in need for such treatment.

In a preferred embodiment, the therapeutically active substances are administered as a combination therapy comprising a substance acting as nicotinic acetylcholine agonist and a substance acting as a monoamine agonist or antagonist or as a monoamine reuptake inhibitor.

In another preferred embodiment, the therapeutic effect is achieved using a substance having the dual activity of a nicotinic acetylcholine agonist and a monoamine agonist or antagonist or a monoamine reuptake inhibitor.

The affective disorder, disease or condition may in particular be depression, anxiety, obsessive compulsive disorder (OCD), panic disorder, obesity, symptoms arising from smoking cessation, or pain, including acute and chronic pain, neuropathic pain, and inflammatory pain.

Nicotinic Acetylcholine Agonists

The nicotinic acetylcholine agonist of the invention may be any ligand that binds to and activates the nicotinic acetylcholine receptor, thereby resulting in a biological response. The potential of a given substance to act as a nicotinic acetylcholine agonist may be determined using standard in vitro binding assays and/or standard in vivo functionality tests.

In a preferred embodiment the nicotinic acetylcholine agonist of the invention show a Ki of less than 1000 nM, preferably less than 100 nM, when determined in a standard human nicotinic receptor ion channel binding and or displacement assay, or an $EC_{50}$ or $IC_{50}$ value of less than 300 µM, preferably less than 100 µM, when determined in a standard functionality assay using a mouse, rat, or human nicotinic receptor ion channel, which ion channel is preferably composed of a combination of $\alpha_{2-9}$ and $\beta_{2-4}$ nAChR subunits, or of homomers of $\alpha$ nAChR subunits.

Nicotinic acetylcholine agonist for use according to the invention include those substances described in e.g. WO 92/21339 (Abbott), WO 94/08992 (Abbott), WO 96/40682 (Abbott), WO 9746554 (Abbott), WO 99/03859 (AstraZeneca), WO 96/15123 (Salk Institute) WO 97/19059 (Sibia), WO 00/10997 (Ortho-McNeil), WO 00/44755 (Abbott), WO 00/34284 (Synthelabo), WO 98/42713 (Synthelabo), WO 99/02517 (Synthelabo), WO 00/34279 (Synthelabo), WO 00/34279 (Synthelabo), WO 00/34284 (Synthelabo), EP 955301 (Pfizer), EP 857725 (Pfizer), EP 870768 (Pfizer), EP 311313 (Yamanouchi Pharmaceutical), WO 97/11072 (Novo Nordisk), WO 97/11073 (Novo Nordisk), WO 98/54182 (NeuroSearch), WO 98/54181 (NeuroSearch), WO 98/54152 (NeuroSearch), WO 98/54189 (NeuroSearch), WO 99/21834 (NeuroSearch), WO 99/24422 (NeuroSearch), WO 00/32600 (NeuroSearch), WO PCT/DK00/00211 (NeuroSearch), WO PCT/DK00/00202 (NeuroSearch), or their foreign equivalents.

Examples of preferred nicotinic acetylcholine agonist according to the invention include nicotine, ethyl nicotine, 3-ethynyl-5-(1-methyl-2-pyrrolidinyl)pyridine (SIB-1765F), 4-[[2-(1-methyl-2-pyrrolidinyl)ethyl]thio]phenol (SIB-1553), (S)-3-ethynyl-5-(1-methyl-2-pyrrolidinyl)-pyridine (SIB-1508Y), 4'-methylnicotine or (2S-trans)-3-(1,4-dimethyl-2-pyrrolidinyl)pyridine (Abbott), 2-methyl-3-[(2S)-2-pyrrolidinylmethoxy]-pyridine (ABT-089), 3-methyl-5-[(2S)-1-methyl-2-pyrrolidinyl]-isoxazole (ABT-418), 5-[(2R)-2-azetidinylmethoxy]-2-chloro- Pyridine (ABT-594), 3-PMP or 3-(1-pyrrolidinyl-methyl)pyrid (RJ Reynold), (3E)-N-methyl-4-(3-pyridinyl)-3-buten-1amine (RJR-2403), anabasein or 3,4,5,6-tetrahydro-2,3'-bipyridine (RJ Reynold), 5-fluoronicotine or (S)-5-fluoro-3-(1-methyl-2-pyrrolidinyl)pyridine (RJ Reynold), MCC or 2-(dimethylamino)ethyl methylcarbamate (Lundbeck), ethyl arecolone or 1-(1,2,5,6-tetrahydro-1-methyl-3-pyridinyl)-1-propanone (Lilly), or isoarecolone or 1-(1,2,3,6-tetrahydro-1-methyl-4-pyridinyl)ethanone (Lilly), AR-R 17779 (AstraZeneca), epibatidine, GTS-21, 1-(6-chloro-3-pyridyl)-homopiperazine, 1-(3-pyridyl)15 homopiperazine, 1-(5-ethynyl-3-pyridyl)-homopiperazine, or salts, free bases, racemates or enantiomers thereof.

Preferred Nicotinic Agonists

In a preferred embodiment the nicotinic acetylcholine agonist for use according to the invention are those disclosed in WO 99/21834 represented by Formula I

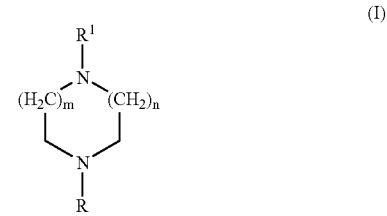

any of its enantiomers or any mixture thereof, isotopes thereof or a pharmaceutically acceptable salt thereof;

wherein n is 1, 2 or 3; and m is 0, 1 or 2; and

R represents hydrogen, alkyl, cycloalkyl, cycloalkylalkyl, alkoxy, acyl or benzyl; and $R^1$ represents 5-bromo-3-pyridyl; 5-bromo-3-pyridyl; 6-chloro-3-pyridyl; 6-bromo-5-methoxy-3-pyridyl; 6-bromo-3-pyridyl; 6-bromo-5-chloro-3-pyridyl; 5,6-dibromo-3-pyridyl; 6-chloro-5-bromo-3-pyridyl; 6-iodo-5-methoxy-3-pyridyl; 5,6-dichloro-3-pyridyl; 5-bromo-6-chloro-2-pyrazinyl; 6-bromo-5-etynyl-3-pyridyl; 6-chloro-5-methoxy-3-pyridyl; 6-phenyl-3-pyridazinyl; 6-chloro-2-pyrazinyl; 6-chloro-3-pyridazinyl; 6-iodo-3-pyridazinyl; 6-(1-benzimidazolyl)-3-pyridazinyl; 2-pyrazinyl; 6-chloro-2-pyrazinyl; 6-phenyl-3-pyridyl; 5-chloro-6-phenyl-3-pyridyl; 5-chloro-6-methyl-3-pyridyl; 5-etynyl-3-pyridyl; 5-bromo-3-pyridyl; 5-methoxy-6-bromo-3-pyridyl; 6-bromo-3-pyridyl; 5-chloro-6-bromo-3-pyridyl; 5,6-dibromo-3-pyridyl; 5-bromo-6-chloro-3-pyridyl; 5-methoxy-6-iodo-3-pyridyl; or 5,6-dichloro-3-pyridyl.

In a more preferred embodiment, the compound for use according to the invention is a chemical compound of Formula I, wherein n and m are 1; and R represents hydrogen, methyl, or 4-tert-butoxycarbonyl; and $R^1$ represents 5-bromo-3-pyridyl; 5-bromo-3-pyridyl; 6-chloro-3-pyridyl; 6-bromo-5-methoxy-3-pyridyl; 6-bromo-3-pyridyl; 6-bromo-5-chloro-3-pyridyl; 5,6-dibromo-3-pyridyl; 6-chloro-5-bromo-3-pyridyl; 6-iodo-5-methoxy-3-pyridyl; 5,6-dichloro-3-pyridyl; 5-bromo-6-chloro-2-pyrazinyl; 6-bromo-5-etynyl-3-pyridyl; 6-chloro-5-methoxy-3-pyridyl; 6-phenyl-3-pyridazinyl; 6-chloro-2-pyrazinyl; 6-chloro-3-pyridazinyl; 6-iodo-3-pyridazinyl; 6-(1-benzimidazolyl)-3-pyridazinyl; 2-pyrazinyl; 6-chloro-2-pyrazinyl; 6-phenyl-3-pyridyl; 5-chloro-6-phenyl-3-pyridyl; 5-chloro-6-methyl-3-pyridyl; 5-etynyl-3-pyridyl; 5-bromo-3-pyridyl; 5-methoxy-6-bromo-3-pyridyl; 6-bromo-3-pyridyl; 5-chloro-6-bromo-3-pyridyl; 5,6-dibromo-3-pyridyl; 5-bromo-6-chloro-3-pyridyl; 5-methoxy-6-iodo-3-pyridyl; or 5,6-dichloro-3-pyridyl.

In its most preferred embodiment, the compound of Formula I is 1-(5-bromo-3-pyridyl)-piperazine;
1-(6-chloro-3-pyridyl)-piperazine;
1-(6-bromo-5-methoxy-3-pyridyl)-piperazine;
1-(6-bromo-3-pyridyl)-piperazine;
1-(6-bromo-5-chloro-3-pyridyl)-piperazine;
1-(5,6-dibromo-3-pyridyl)-piperazine;
1-(6-chloro-5-bromo-3-pyridyl)-piperazine;
1-(6-iodo-5-methoxy-3-pyridyl)-piperazine;
1-(5,6-dichloro-3-pyridyl)-piperazine;
1-(5-bromo-6-chloro-2-pyrazinyl)-piperazine;
1-(6-bromo-5-etynyl-3-pyridyl)-piperazine;
1-(6-chloro-5-methoxy-pyridyl)-piperazine;
1-(6-phenyl-3-pyridazinyl)-piperazine;
1-(6-chloro-2-pyrazinyl)-piperazine;
1-(6-chloro-3-pyridazinyl)-piperazine;
1-(6-iodo-3-pyridazinyl)-piperazine;
1-[6-(1-benzimidazolyl)-3-pyridazinyl]-piperazine;
1-(2-pyrazinyl)-piperazine;
1-(6-chloro-2-pyrazinyl)-4-methyl-piperazine;
1-(6-phenyl-3-pyridyl)-piperazine;
1-(5-chloro-6-phenyl-3-pyridyl)-piperazine;
1-(5-chloro-6-methyl-3-pyridyl)-4-tert-butoxycarbonyl-piperazine; or
1-(5-etynyl-3-pyridyl)-piperazine;

or an enantiomer or a mixture of its enantiomers, or an isotope thereof or a pharmaceutically acceptable salt thereof.

In another preferred embodiment, the compound for use according to the invention is a chemical compound of Formula 1, wherein n is 2; and m is 1; and R represents hydrogen, methyl, or 4-tert-butoxycarbonyl; and $R^1$ represents 5-bromo-3-pyridyl; 5-bromo-3-pyridyl; 6-chloro-3-pyridyl; 6-bromo-5-methoxy-3-pyridyl; 6-bromo-3-pyridyl; 6-bromo-5-chloro-3-pyridyl; 5,6-dibromo-3-pyridyl; 6-chloro-5-bromo-3-pyridyl; 6-iodo-5-methoxy-3-pyridyl; 5,6-dichloro-3-pyridyl; 5-bromo-6-chloro-2-pyrazinyl; 6-bromo-5-etynyl-3-pyridyl; 6-chloro-5-methoxy-3-pyridyl; 6-phenyl-3-pyrdazinyl; 6-chloro-2-pyrazinyl; 6-chloro-3-pyridazinyl; 6-iodo-3-pyridazinyl; 6-(1-benzimidazolyi)-3-pyridazinyl; 2-pyrazinyl; 6-chloro-2-pyrazinyl; 6-phenyl-3-pyridyl; 5-chloro-6-phenyl-3-pyridyl; 5-chloro-6-methyl-3-pyridyl; 5-etynyl-3-pyridyl; 5-bromo-3-pyridyl; 5-methoxy-6-bromo-3-pyridyl; 6-bromo-3-pyridyl; 5-chloro-6-bromo-3-pyridyl; 5,6-dibromo-3-pyridyl; 5-bromo-6-chloro-3-pyridyl; 5-methoxy-6-iodo-3-pyridyl; or 5,6-dichloro-3-pyridyl.

In its most preferred embodiment, the compound of Formula I is 1-(5-bromo-3-pyridyl)-homopiperazine;
1-(6-chloro-3-pyridyl)-homopiperazine;
1-(5-methoxy-6-bromo-3-pyridyl)-homopiperazine;
1-(6-bromo-3-pyridyl)-homopiperazine;
1-(5-chloro-6-bromo-3-pyridyl)-homopiperazine;
1-(5,6-dibromo-3-pyridyl)-homopiperazine;
1-(5-bromo-6-chloro-3-pyridyl)-homopiperazine;
1-(5-methoxy-6-iodo-3-pyridyl)-homopiperazine; or
1-(5,6-dichloro-3-pyridyl)-homopiperazine;

or an enantiomer or a mixture of its enantiomers, or an isotope thereof or a pharmaceutically acceptable salt thereof.

Monoaminergic Substances

The monoamine activity may be obtained using any monoaminergic substance showing monoamine agonistic or antagonistic or monoamine reuptake inhibiting activity.

The monoamine reuptake inhibitor for use according to the invention may in particular be a mixed monoamine reuptake inhibitor, a noradrenalin/dopamin uptake inhibitor, a classical tricyclic antidepressive agent, or a selective serotonin reuptake inhibitor (SSR1).

Serotonergic drugs for use according to the invention include Fenfluramine, Dexfenfluramine, Tryptophan, Chlorimipraqmine, Cyanimipramine, Fluoxetine, Paroxetine, Citalopram, Femoxitine, Cianopramine, Sertaline, Sibutramine, Venlafaxine, ORG 6582, RU 25591, LM 5008, DU 24565, Indalpine, CGP 6085/A, WY 25093, Alaprociate, Zimelidine, Trazodone, Amitriptyline, Imipramine, Desipramine, Mirtazapine, Trimipramine, Doxepin, Protriptylin, Nortriptylin, Dibenzoxazepine, Deprenyl, Isocarboxazide, Pheneizine, Tranylcypromine, Furazolidone, Procarbazine, Moclobemide, Brofaromin, Nefazodone, Bupropion, MK-212, DOI, m-CPP, RO 60-0175/ORG 35030, RO 60-0332/ORG 35035, RO 60-0175, ORG 12962, RO 60-0332, α-methyl-5HT, TFMPP, Bufotenin, RU 24969, Quipazine, 5-carboxyamidotryptamine, Sumatripan, CGS 12066, 8-OH-DPAT, (S)-2-(chloro-5-fluoro-indol-1-yl)-1-methylethylamine, (S)-2-(4,4,7-trimethyl-1,4-dihydro-indeno(1,2-b)pyrrol-1-yl)-1-methylethylamine, SB 206553, and pharmaceutically acceptable salts thereof.

Examples of preferred serotonergic agonistic drugs include MK-212, DOI, m-CPP, RO 60-0175/ORG 35030, RO 60-0332/ORG 35035, ORG 12962, (S)-2-(chloro-5- fluoro-indol-1-yl)-1-methylethylamine, (S)-2-(4,4,7-trimethyl-1,4-dihydro-indeno(1,2-b)pyrrol-1-yl)-1-methylethylamine, and SB 206553.

Examples of preferred of mixed monoamine reuptake inhibiting drugs include those described in WO 97/16451 (NeuroSearch) and WO 97/13770 (NeuroSearch), or their foreign equivalents. The most preferred mixed monoamine reuptake inhibiting drugs include (1S,3S,4S,5S,8R)-3-(3,4-dichlorophenyl)-7-azatricyclo[5.3.0.0]decan-5-ol.

Examples of preferred of NA/DA-uptake inhibitors include drugs like Venlafaxin, Bupropion, Nomifensine, Minacipram, Reboxetin.

Examples of preferred of classic tricyclic antidepressiva include drugs like Imipramin, Amitriptyline, Clomipramine, Doxepin, Amoxapine, Desipramine, Maprotiline, Nortriptyline and Protriptyline.

In its most preferred embodiment the monoamine reuptake inhibitor of the invention is a mixed monoamine reuptake inhibitor or a selective serotonin reuptake inhibitor (SSR1). Examples of preferred of SSR1's include drugs like Norzimeldine, Fluoxetine, Clomipramine, Sertraline, Fluvoxamine, Alaproclate, (−)-trans-5-(4-p-fluorophenyl-3-piperidylmethoxy)-1,3-benzodioxole (Paroxetine), and 1-[3-(dimethylamino)propyl]-1-(p-fluorophenyl)-1,3-dihydroisobenzofuran-5-carbonitrile (Citalopram), and Nefazodone.

Chemical Substances of "Dual Action"

In another embodiment, the therapeutic effect is achieved using a substance having the dual activity of a nicotinic acetylcholine agonist and a monoamine agonist or antagonist or a monoamine reuptake inhibitor. A chemical compound for use according to the invention having this dual activity may in particular be a diazabicycloalkane derivative as described in WO 00/66586 and in co-pending International Patent Application No. PCT/DK01/00432, and represented by the general Formula II

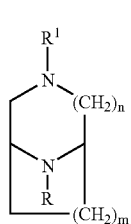
(II)

or a dimer thereof represented by any of Formulas III, IV or V

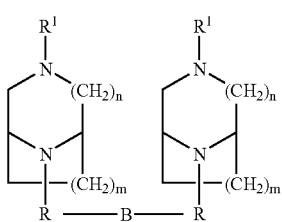
(III)

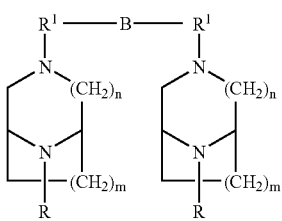
(IV)

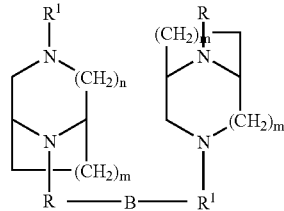
(V)

wherein, n is 2; and m is 1; and one of R and $R^1$ represents hydrogen or alkyl; and the other of R or $R^1$ represents a phenyl group, a naphthyl group or a quinolinyl group, which groups may be substituted once or twice with chloro, fluoro, trifluoromethyl, methoxy or trifluoromethoxy, and B represents a bridging linker, e.g. ethyleneglycol.

In a more preferred embodiment the compound for use according to the invention is a diazabicycloalkane derivative of Formula II, wherein one of R or $R^1$ represents hydrogen or methyl, and the other of R and $R^1$ represents 2-naphthalyl; 2-quinolinyl; 3,4-dichlorophenyl; 6-quinolinyl; 4-fluorophenyl; 3-fluorophenyl; 4-trifluoromethoxyphenyl; 3-trifluoromethoxyphenyl; phenyl; or 3,4-dichlorophenyl.

In a most preferred embodiment the compound for use according to the invention is a diazabicycloalkane derivative of Formula II, which is (±) 3-(2-naphthalyl)-9-methyl-3,9-diazabicyclo-[4.2.1]-nonane;

(±) 3-(2-quinolinyl)-9-methyl-3,9-diazabicyclo-[4.2.1]-nonane;

(±) 3-(3,4-dichlorophenyl)-9-methyl-3,9-diazabicyclo-[4.2.1]-nonane;

(±) 3-(6-quinolinyl)-9-methyl-3,9-diazabicyclo-[4.2.1]-nonane;

(±) 3-(4-fluorophenyl)-9-methyl-3,9-diazabicyclo-[4.2.1]-nonane;

(±) 3-(3-fluorophenyl)-9-methyl-3,9-diazabicyclo-[4.2.1]-nonane;

(±) 3-(4-trifluoromethoxyphenyl)-9-methyl-3,9-diazabicyclo-[4.2.1]-nonane;

(±) 3-(3-trifluoromethoxyphenyl)-9-methyl-3,9-diazabicyclo-[4.2.1]-nonane;

(±) 3-(phenyl)-9-methyl-3,9-diazabicyclo-[4.2.1]-nonane; or (±) 3-(3,4-dichlorophenyl)-9-H-3,9-diazabicyclo-[4.2.1-]-nonane;

or an enantiomer or a mixture of its enantiomers, or an isotope thereof or a pharmaceutically acceptable salt thereof.

In another preferred embodiment the compound for use according to the invention is a diazabicycloalkane derivative of Formula IV or V, which is O,O'-bis-[5-(9-Methyl-3,9-diazabicyclo-[4.2.1]-nonan-3-yl)-3-pyridyl]-ethyleneglycol;

or an enantiomer or a mixture of its enantiomers, or an isotope thereof or a pharmaceutically acceptable salt thereof.

In yet another preferred embodiment the therapeutic effect is achieved using a substance having the dual activity of a nicotinic acetylcholine agonist and a monoamine agonist or antagonist or a monoamine reuptake inhibitor. A chemical compound for use according to the invention having dual activity may in particular be an 8-azabicyclo[3.2.1]oct-2-ene derivative of Formula VI,

any of its enantiomers or any mixture of its enantiomers, or a pharmaceutically acceptable salt thereof;
wherein
R is hydrogen, alkyl, alkenyl, cycloalkyl, cyanoalkyl, phenyl, naphthyl or benzyl; and
$R^1$ is

wherein $R^2$ is hydrogen, alkyl, cycloalkyl, or amino; or furanyl, thienyl, pyrrolyl, oxazolyl, isoaxzolyl, imidazolyl, pyridyl, pyrimidinyl or thiazolyl, which heteroaryl group is optionally substituted one or more times with substituents selected from the group consisting of alkyl, cycloalkyl, alkoxy, cyanoalkyl, halogen, $CF_3$, $OCF_3$, CN, amino, nitro, and furyl; or naphthyl, indolyl, benzofuranyl, benzothienyl, benzimidazolyl, benzothiazolyl, quinolinyl, isoquinolinyl or thienothienyl, which bicyclic group is optionally substituted one or more times with substituents selected from the group consisting of alkyl, cycloalkyl, alkoxy, cyanoalkyl, halogen, $CF_3$, $OCF_3$, CN, amino, nitro and furyl.

In a more preferred embodiment R of Formula VI represents hydrogen, methyl, ethyl, allyl, cyanomethyl, or benzyl; and $R^1$ of Formula VI represents acetyl, 3-pyridyl, 3-(6-methoxy)pyridyl, 3-(6-chloro)pyridyl, 2-thiazolyl, 3-thienyl, 2-thienyl, 2-(3-methoxymethyl)thienyl, 2-(3-bromo) thienyl, 2-(3,4-dibromo)thienyl, 2-furyl, 3-furyl, 2-(3-bromo)thienyl), 3-chloro-thien-2-yl, 5-indolyl, 3-(3-furyl)-2-thienyl, 3-quinolinyl, 3-benzofuryl, 2-benzofuryl, 3-benzothienyl, 2-benzothienyl, 2-benzothiazolyl, 2-thieno [3.2-b]thienyl, thieno[2.3-b]thienyl, 2-(3-bromo)benzofuryl or 2-(3-bromo)benzothienyl.

In it most preferred embodiment the 8-azabicyclo[3.2.1] oct-2-ene derivative of Formula VI is (±)-3-(2-benzothienyl)-8-H-8-azabicyclo[3.2.1]oct-2-ene;

(±)-3-(2-benzothienyl)-8-ethyl-8-azabicyclo[3.2.1]oct-2-ene;

(±)-8-allyl-3-(2-benzothienyl)-8-azabicyclo[3.2.1]oct-2-ene;

(±)-8-allyl-3-(2-benzothienyl)-8-azabicyclo[3.2.1]oct-2-ene;

(±)-8-allyl-3-[2-(3-bromothienyl)]-8-azabicyclo[3.2.1] oct-2-ene;

(±)-3-(2-benzothienyl)-8-cyanomethyl-8-azabicyclo [3.2.1]oct-2-ene;

(±)-3-[2-(3,4-dibromothienyl)]-8-methyl-8-azabicyclo [3.2.1]oct-2-ene; or (±)-3-(5-indolyl)-8-methyl-8-azabicyclo[3.2.1]oct-2-ene;

or an enantiomer or a mixture of its enantiomers, or an isotope thereof or a pharmaceutically acceptable salt thereof.

Definition of Substituents

In the context of this invention halogen represents a fluorine, a chlorine, a bromine or an Iodine atom. Thus, a trihalogenmethyl group represents e.g. a trifluoromethyl group, a trichloromethyl group and similar trihalogen-substituted methyl groups.

In the context of this invention an alkyl group designates a univalent saturated, straight or branched hydrocarbon chain. The hydrocarbon chain preferably contain of from one to eighteen carbon atoms ($C_{1-18}$-alkyl), more preferred of from one to six carbon atoms ($C_{1-6}$alkyl; lower alkyl), including pentyl, isopentyl, neopentyl, tertiary pentyl, hexyl and isohexyl. In a preferred embodiment alkyl represents a $C_{1-4}$-alkyl group, including butyl, isobutyl, secondary butyl, and tertiary butyl. In another preferred embodiment of this invention alkyl represents a $C_{1-3}$-alkyl group, which may in particular be methyl, ethyl, propyl or isopropyl.

In the context of this invention an alkenyl group designates a carbon chain containing one or more double bonds, including di-enes, tri-enes and poly-enes. In a preferred embodiment the alkenyl group of the invention comprises of from two to eight carbon atoms ($C_{2-8}$-alkenyl), more preferred of from two to six carbon atoms ($C_{2-6}$-alkenyl), including at least one double bond. In a most preferred embodiment the alkenyl group of the invention is ethenyl; 1- or 2-propenyl; 1-, 2- or 3-butenyl, or 1,3-butdienyl; 1-, 2-, 3-, 4- or 5-hexenyl, or 1,3-hexdienyl, or 1,3,5-hextrienyl; 1-, 2-, 3-, 4-, 5-, 6-, or 7-octenyl, or 1,3-octdienyl, or 1,3,5-octtrienyl, or 1,3,5,7-octtetraenyl.

In the context of this invention a cycloalkyl group designates a cyclic alkyl group, preferably containing of from three to seven carbon atoms ($C_{3-7}$-cycloalkyl), including cyclopropyl, cyclobutyl, cyclopentyl, cyclohexyl and cycloheptyl.

In the context of this invention a cycloalkyl-alkyl group designates a cycloalkyl group as defined above, which cycloalkyl group is substituted on an alkyl group as also defined above. Examples of preferred cycloalkyl-alkyl groups of the invention include cyclopropylmethyl and cyclopropylethyl.

In the context of this invention an alkoxy group designates an "alkyl-O-" group, wherein alkyl is as defined above.

In the context of this invention an acyl group designates a carboxy group (—COOH) or an alkyl-carbonyl group (alkyl-CO—), wherein alkyl is as defined above. Examples of preferred acyl groups of the invention include carboxy, acetyl, propionyl, and 4-tert-butoxycarbonyl.

Pharmaceutical Compositions

Viewed from another aspect the invention relates to the use of a nicotinic acetylcholine agonist and a monoamine reuptake inhibitor for the manufacture of a medicament for the treatment, prevention or alleviation of an affective disorder, disease or condition in a subject, including a human.

The pharmaceutical composition according to the invention therefore comprises a therapeutically effective amount of a nicotinic acetylcholine agonist and a monoamine agonist or antagonist or monoamine reuptake inhibitor, together with at least one pharmaceutically acceptable carrier or diluent.

In a preferred embodiment, the pharmaceutical composition comprises a substance acting as nicotinic acetylcholine agonist and a substance acting as a monoamine agonist or antagonist or monoamine reuptake inhibitor.

In another preferred embodiment, however, the pharmaceutical composition comprises a substance having the dual activity of a nicotinic acetylcholine agonist and a monoamine agonist or antagonist or monoamine reuptake inhibitor.

While a chemical compound of the invention for use in therapy may be administered in the form of the raw chemical compound, it is preferred to introduce the active ingredient, optionally in the form of a physiologically acceptable salt, in a pharmaceutical composition together with one or more adjuvants, excipients, carriers, buffers, diluents, and/or other customary pharmaceutical auxiliaries.

In a preferred embodiment, the invention provides pharmaceutical compositions comprising the chemical compound of the invention, or a pharmaceutically acceptable salt or derivative thereof, together with one or more pharmaceutically acceptable carriers therefore, and, optionally, other therapeutic and/or prophylactic ingredients, know and used in the art. The carrier(s) must be "acceptable" in the sense of being compatible with the other ingredients of the formulation and not harmful to the recipient thereof.

The pharmaceutical composition of the invention may be administered by any convenient route, which suits the desired therapy. Preferred routes of administration include oral administration, in particular in tablet, in capsule, in dragé, in powder, or in liquid form, and parenteral administration, in particular cutaneous, subcutaneous, intramuscular, or intravenous injection. The pharmaceutical composition may be prepared by the skilled person using standard and conventional techniques appropriate to the desired formulation. When desired, compositions adapted to give sustained release of the active ingredient may be employed.

Further details on techniques for formulation and administration may be found in the latest edition of *Remington's Pharmaceutical Sciences* (Maack Publishing Co., Easton, Pa.).

The pharmaceutical composition of the invention preferably is for use in the treatment, prevention or alleviation of an affective disorder, disease or condition in a subject. The affective disorder, disease or condition may in particular be depression, anxiety, obsessive compulsive disorder (OCD), panic disorder, or pain.

The actual dosage depend on the nature and severity of the disease being treated, and is within the discretion of the physician, and may be varied by titration of the dosage to the particular circumstances of this invention to produce the desired therapeutic effect. However, it is presently contemplated that pharmaceutical compositions containing of from about 0.01 to about 500 mg of active ingredient per individual dose, preferably of from about 0.1 to about 100 mg, most preferred of from about 1 to about 10 mg, are suitable for therapeutic treatments.

The active ingredient may be administered in one or several doses per day. A satisfactory result can, in certain instances, be obtained at a dosage as low as 0.1 µg/kg i.v. and 1 µg/kg p.o. The upper limit of the dosage range is presently considered to be about 10 mg/kg i.v. and 100 mg/kg p.o. Preferred ranges are from about 0.1 µg/kg to about 10 mg/kg/day i.v., and from about 1 µg/kg to about 100 mg/kg/day p.o.

EXAMPLES

The invention is further illustrated with reference to the following examples, which are not intended to be in any way limiting to the scope of the invention as claimed.

Example 1

Preparatory Example

General

All reactions involving air sensitive reagents or intermediates were performed under nitrogen and in anhydrous solvents. Magnesium sulphate was used as drying agent in the workup-procedures and solvents were evaporated under reduced pressure.

Method A 1-(5-Bromo-3-pyridyl)-piperazine Fumaric Acid Salt (Compound 1A1)

A mixture of 3,5-dibromopyridine (100 g, 422 mmol) and piperazine (72.7 g, 844 mmol) was stirred at 130° C. for 100 hours. Water (400 ml) was added and the pH was adjusted to 7 by adding hydrochloric acid (4 M). The aqueous phase was washed three times with ethyl acetate (3×600 ml). The aqueous mixture was made alkaline by adding sodium hydroxide (200 ml, 4 M). The aqueous mixture was extracted four times with diethyl ether (4×500 ml). The product was isolated as free base. Yield 44 g (43%). The corresponding salt was obtained by addition of a diethyl ether and methanol mixture (9:1) saturated with fumaric acid. Mp 185.0° C.

1-(5-Chloro-3-pyridyl)-piperazine fumaric acid salt (Compound 1A2)

Was prepared according to method A. Mp 195-196° C.

Method B 1-(6-Bromo-5-methoxy-3-pyridyl)-piperazine Fumaric Acid Salt (Compound 1B1)

A mixture of 3-chloro-5-methoxypyridine (40.0 g, 0.279 mol), piperazine (48.0 g, 0.557 mol), potassium-tert-butoxide (62.5 g, 0.557 mol) and tetrakis-(triphenylphosphine) palladium(0) (1.6 g, 1.39 mmol) was refluxed for 2 hours. The workup procedure was performed according to method A. 1-(5-Methoxy-3-pyridyl)piperazine fumaric acid salt was isolated as intermediate product. Yield 22.6 g (26%). A mixture of 1-(5-methoxy-3-pyridyl)-piperazine fumaric acid salt (23.1 g, 74.7 mmol), aqueous sodium hydrogen carbonate (224 ml, 1 M), di-tert-butyldicarbonate (16.3 g, 74.7 mmol) and dichloromethane (200 ml) was stirred at room temperature for 1 hour. The phases were separated. The organic phase gave 4-tert-butoxycarbonyl-1-(5-methoxy-3-pyridyl)-piperazine in quantitative yield. N-Bromosuccinimide (1.82 g, 10.2 mmol) was added to a mixture of 4-tert-butoxycarbonyl-1-(5-methoxy-3-pyridyl)-piperazine (3.0 g, 10.2 mmol) and acetonitrile (50 ml) at 0° C. The reaction was allowed to reach room temperature and was stirred for 2 hours. Aqueous sodium hydroxide (100 ml, 4 M) was added followed by extraction twice with ethyl acetate (2×100 ml). Chromatography on silica gel with ethyl acetate:petroleum (1:3) gave 4-tert-butoxycarbonyl-1-(6-bromo-5-methoxy-3-pyridyl)-piperazine as free base. Yield 2.6 g, 68%. This compound (2.32 g, 6.23 mmol) was deprotected by stirring with a mixture of trifluoroacetic acid (4.8 ml) and dichloromethane (30 ml) for 6 hours. The mixture was evaporated, and aqueous sodium hydroxide (100 ml, 1 M) was added. The mixture was extracted three times with ethyl acetate (3×100) and gave the title compound as the free base. The corresponding salt was obtained by addition of a diethyl ether and methanol mixture (9:1) saturated with fumaric acid in quantitative yield. Mp 202-218° C.

1-(6-Iodo-5-methoxy-3-pyridyl)-piperazine Fumaric Acid Salt (Compound 1B2)

Was prepared according to method B from 1-(5-methoxy-3-pyridyl)-piperazine. Using N-iodo succinimide instead of N-bromo succinimide. Mp 209.5° C.

1-(6-Bromo-3-pyridyl)-piperazine Fumaric Acid Salt (Compound 1B3)

Was prepared according to method B from 1-(3-pyridyl)-piperazine. Mp 170.8-171.6° C.

1-(6-Bromo-5-chloro-3-pyridyl)-piperazine Fumaric Acid Salt (Compound 1B4)

Was prepared according to method B from 1-(5-chloro-3-pyridyl)-piperazine. Mp 199.6-200.2° C.

1-(5.6-Dibromo-3-pyridyl)-piperazine Fumaric Acid Salt (Compound 1B5)

Was prepared according to method B from 1-(5-bromo-3-pyridyl)-piperazine. Mp 199.5° C.

1-(5-Bromo-6-chloro-2-pyrazinyl)-piperazine Fumaric Acid Salt (Compound 1B6)

Was prepared according to method B from 1-(6-chloro-2-pyrazinyl)-piperazine. Mp 185.6° C.

1-(6-Bromo-5-etynyl-3-pyridyl)-piperazine Fumaric Acid Salt (Compound 1B7)

Was prepared according to method B from 1-(5-etynyl-3-pyridyl)-piperazine. Mp 210.4° C.

Method C 1-(5-Bromo-6-chloro-3-pyridyl)-piperazine Fumaric Acid Salt (Compound 1C1)

A mixture of 1-(5,6-dibromo-3-pyridyl)-piperazine (1.5 g, 4.7 mmol) and concentrated hydrochloric acid (30 ml) was stirred at reflux for 52 hours. The mixture was evaporated. Aqueous sodium hydroxide (100 ml, 1 M) was added followed by extraction with ethyl acetate (2×50 ml). The corresponding salt was obtained by addition of a diethyl ether and methanol mixture (9:1) saturated with fumaric acid. Yield 1.0 g (54%). Mp 181.2-185.9° C.

1-(5,6-Dichloro-3-pyridyl)-piperazine Fumaric Acid Salt (Compound 1C2)

Was prepared according to method C from 1-(6-bromo-5-chloro-3-pyridyl)-piperazine. Mp 180.3° C.

1-(6-Chloro-3-pyridyl)-piperazine Dihydrochloric Acid Salt (Compound 1C3)

Was prepared from 1-(6-bromo-3-pyridyl)-piperazine according to method C. Mp 271-273° C.

1-(6-Chloro-5-methoxy-3-pyridyl)-piperazine Fumaric Acid Salt (Compound 1C4)

Was prepared from 1-(6-bromo-5-methoxy-3-pyridyl)-piperazine according to method C. Mp 201.3-201.6° C.

Method D (±)-3-(2-Benzothienyl)-8-H-8-azabicyclo[3.2.1]oct-2-ene (Compound 1D1)

A mixture of (±)-3-(2-benzothienyl)-8-methyl-8-azabicyclo[3.2.1]oct-2-ene (24.4 g, 0.0955 mol), 1-chloroethylchloroformate (15.5 ml, 0.143 mol) and xylene (200 ml) was heated and stirred at reflux temperature for 24 hours. Methanol (300 ml) was added followed by stirring and heating at reflux temperature for 22 hours. The mixture was cooled to room temperature and the product was filtered. The crude product was recrystallised from diethyl ether. Yield 16 g (69%). Mp 252-259° C.

(±)-3-(2-Benzothienyl)-8-ethyl-8-azabicyclo[3.2.1]oct-2-ene Fumaric Acid Salt (Compound 1D2)

A mixture of (±)-3-(2-benzothienyl)-8-H-8-azabicyclo[3.2.1]oct-2-ene (2.00 g, 8.29 mmol), bromoethane (0.74 ml, 9.94 mmol), diisopropylethylamine (2.9 ml, 16.6 mmol) and dimethylformamide (30 ml) was stirred at 80° C. for 7 hours. Aqueous sodium hydroxide (50 ml, 1 M) was added and the mixture was extracted three times with ethyl acetate (3×50 ml). Chromatography of this crude mixture on silica gel with dichloromethane, methanol and conc. ammonia (89:10:1) gave the title compound. The corresponding salt was obtained by addition of a diethyl ether and methanol mixture (9:1) saturated with fumaric acid. Yield 1.00 g, 31%. Mp 176.9° C.

Method E (±)-8-Allyl-3-(2-benzothienyl)-8-azabicyclo[3.2.1]oct-2-ene (Compound 1E1))

A mixture of (±)-3-(2-benzothienyl)-8-H-8-azabicyclo[3.2.1]oct-2-ene (2.00 g, 8.29 mmol), 3-bromo-1-propene (0.74 ml, 9.11 mmol), diisopropylethylamine (2.9 ml, 16.6 mmol) and dimethylformamide (30 ml) was stirred at 80° C. for 24 hours. Aqueous sodium hydroxide (50 ml, 1 M) was added and the mixture was extracted three times with ethyl acetate (3×50 ml). The crude product was solved in diethyl ether (50 ml) and was washed with aqueous sodium hydroxide (50 ml, 1 M). Yield 1.44 g, 62%. Mp 60.6-62.6° C.

(±)-8-Allyl-3-[2-(3-bromothienyl)]-8-azabicyclo[3.2.1]oct-2-ene (Compound 1E2

Was prepared according to method F. The compound was isolated as an oil.

(±)-3-(2-Benzothienyl)-8-cyanomethyl-8-azabicyclo[3.2.1]oct-2-ene fumaric acid salt (Compound 1E3)

A mixture of (±)-3-(2-benzothienyl)-8-H-8-azabicyclo[3.2.1]oct-2-ene (2.00 g, 8.29 mmol), bromoacetonitrile (0.63 ml, 9.11 mmol), diisopropylethylamine (2.9 ml, 16.6 mmol) and dimethylformamide (30 ml) was stirred at 80° C. for 2.5 hour. Aqueous sodium hydroxide (50 ml, 1 M) was added and the mixture was extracted three times with ethyl acetate (3×50 ml). Chromatography of this crude mixture on silica gel with dichloromethane:ethyl acetate (1:1) gave the title compound. The corresponding salt was obtained by addition of a diethyl ether and methanol mixture (9:1) saturated with fumaric acid. Yield 1.00 g, 31%. Mp 176.9° C.

Method F (±)-3-[2-(3,4-Dibromothienyl)]-8-methyl-8-azabicyclo[3.2.1]oct-2-ene Fumaric Acid Salt (Compound 1F1)

To a mixture of 3,4-dibromothiophene (11.7 g, 48.4 mmol) and tetrahydrofuran was added at −80° C.: lithium-diisopropylamide (27 ml, 2 M in heptane/tetrahydrofuran/ethylbenzene). The mixture was stirred for 1 h at −80° C. Tropinone (6.73 g, 48.4 mmol) solved in tetrahydrofuran (50 ml) was added at −80° C. and was stirred for 1 h at −80° C. The reaction-mixture was allowed to reach room temperature. Water (10 ml) was added, followed by aqueous sodium hydroxide (50 ml, 1 M). The tetrahydrofuran was evaporated. The aqueous mixture was extracted with ethyl acetate (3×50 ml). The intermediate product: endo & exo-3-[2-(3, 4-Dibromo-thienyl)]-3-hydroxy-8-methyl-8-azabicyclo [3.2.1]octane. To an ice-cool mixture of endo & exo-3-[2-(3,4-dibromo-thienyl)]-3-hydroxy-8-methyl-8-azabicyclo [3.2.1]octane (7.40 g, 19.4 mmol) and tetrahydrofuran (100 ml) was added: thionyl chloride (25 ml). The mixture was stirred at 66° C. for 2.5 h. The mixture was evaporated and water (100 ml) was added. The mixture was extracted with diethyl ether (3×100 ml).

Chromatography of this crude mixture on silica gel with dichloromethane, methanol and conc. ammonia (89:10:1) gave the title compound. Yield 5.26 g, 75%. The corresponding salt was obtained by addition of a diethyl ether and methanol mixture (9:1) saturated with fumaric acid. Mp 176.9° C.

Starting Material:

(±)-8-Methyl-3-trifluoromethanesulfonyl-oxy-8-azabicyclo [3.2.1]oct-2-ene (Compound 1F2)

To 8-methyl-8-azabicyclo[3.2.1]octan-3-one (12.65 g, 90.9 mmol) in tetrahydrofuran (300 ml), was added at −70° C.; sodium bis(trimethylsilyl)amide in tetrahydrofuran (77.5 ml, 77.5 mmol). The reaction mixture was stirred for 30 min at −70° C. N-phenyl-bis(trifluoromethane-sulfonamide) (32.5 g, 90.9 mmol) in tetrahydrofuran (200 ml) was added at −70° C. The reaction mixture was allowed to reach room temperature slowly and was stirred over night. Aqueous sodium hydroxide (0.1 M, 500 ml) was added and the mixture was extracted twice with ethyl acetate (200 ml). Chromatography on silica gel with dichloromethane and 10% ethanol as solvent gave the title compound as an oil. Yield 16.2 g, 45%.

(±)-3-(5-Indolyl)-8-methyl-8-azabicyclo[3.2.1]oct-2-ene (Compound 1F3)

A mixture of (±)-8-methyl-3-trifluoromethanesulfonyl-oxy-8-azabicyclo[3.2.1]oct-2-ene (3.37 g, 12.4 mmol), 5-indolylboronic acid (2.00 g, 12.4 mmol), lithium chloride (1.58 g, 37.3 mmol), tetrakistriphenylphosphinepalladium (0) (0.43 mg, 0.4 mmol), potassium carbonate (5.14 g, 37.3 mmol), 1,3-propandiol (2.84 g, 37.3 mmol) and 1,2-dimethoxyethane (40 ml) was stirred and heated at reflux for 20 hours. Aqueous odium hydroxide (100 ml, 1 M) was added. The mixture was extracted twice with diethyl ether. Chromatography of this crude mixture on silica gel with dichloromethane, ethanol and conc. ammonia (89:10:1) gave the title compound. The corresponding salt was obtained by addition of a diethyl ether and methanol mixture (9:1) saturated with fumaric acid. Yield 130 mg, 3.0%. Mp 167.4-178.0° C.

Method G 1-(6-Phenyl-3-pyridazinyl)-piperazine Fumaric Acid Salt (Compound 1G1)

A mixture of 3-chloro-6-phenyl-pyridazine (1.0 g, 5.25 mmol), piperazine. (2.26 g, 26.2 mmol) and toluene (50 ml) was stirred at reflux overnight. The pH was adjusted to 6 with aqueous hydrochloric acid (1 M) and the aqueous phase was washed with methylene chloride (3×50 ml). Aqueous sodium hydroxide (100 ml, 2 M) was added. The mixture was extracted with methylene chloride (3×50 ml). The corresponding salt was obtained by addition of a diethyl ether and methanol mixture (9:1) saturated with fumaric acid. Yield 1.0 g, 53%. Mp 196.4-199.1° C.

1-(6-Chloro-2-pyrazinyl)-piperazine Hydrochloric Acid Salt (Compound 1G2)

Was prepared according to method G. Mp 285.7° C.

1-(6-Chloro-3-pyridazinyl)-piperazine Fumaric Acid Salt (Compound 1 G3)

Was prepared according to method G. Mp 193° C.

1-(6-Iodo-3-pyridazinyl)-piperazine Fumaric Acid Salt (Compound 1G4)

Was prepared according to method G. Mp 187-190° C.

1-[6-(1-Benzimidazolyl)-3-pyridazinyl]-piperazine Fumaric Acid Salt (Compound 1G5)

Was prepared according to method G. Mp 217.0° C.

1-(2-pyrazinyl)-piperazine Fumaric Acid Salt (Compound 1G6)

Was prepared from 1-(6-Chloro-2-pyrazinyl)-piperazine by hydrogenation, using palladium on carbon as catalyst. Mp 177.1° C.

Method H 1-(6-Chloro-2-pyrazinyl)-4-methyl-piperazine Fumaric Acid Salt (Compound 1H1)

1-(6-Chloro-2-pyrazinyl)-piperazine (5.0 g, 25.2 mmol), formaldehyde (37 wt %, d=1.083, 38 ml, 0.503 mol) and formic acid (d=1.22, 19 ml, 0.503 mol) was stirred at reflux for 6 hours. The mixture was evaporated. Aqueous sodium hydroxide (1 M, 100 ml) was added. The mixture was extracted with diethyl ether (3×100 ml). Chromatography of this crude mixture on silica gel with dichloromethane, methanol and conc. ammonia (89:10:1) gave the title compound. Yield 3.97 g (74%) The corresponding salt was obtained by addition of a diethyl ether and methanol mixture (9:1) saturated with fumaric acid. Mp 176.9° C.

Method I 1-(6-Phenyl-3-pyridyl)-piperazine Fumaric Acid Salt (Compound 1I1)

A mixture of 1-(6-bromo-3-pyridyl)-4-tert-butoxycarbonylpiperazine (1.0 g, 2.9 mmol), phenyl boronic acid (1.06 g, 8.8 mmol), aqueous potassium carbonate (4.3 ml, 8.7 mmol), water (4.3 ml), isopropanol (0.66 ml, 8.7 mmol), 1.2-dimethoxyethane (10 ml) and palladium (0) tetrakis triphenylphosphine (66 mg, 0.058 mmol) was stirred at reflux for 4 days. Aqueous sodium hydroxide (50 ml) was added and the mixture was extracted with methylene chloride (3×50 ml). Chromatography of this crude mixture on silica gel with dichloromethane, methanol and conc. ammonia (89:10:1) gave 1-(6-phenyl-3-pyridyl)-4-tert-butoxycarbonylpiperazine. The intermediate (0.80 g, 2.4 mmol), trifluoroacetic acid (1.8 ml, 23.6 mmol) and dichloromethane (10 ml) was stirred for 1.5 hour. The mixture was evaporated. Aqueous sodium hydroxide (50 ml, 1 M) was added and the mixture was extracted with diethyl ether (3×50 ml). The corresponding salt was obtained by addition of a diethyl ether and methanol mixture (9:1) saturated with fumaric acid. Mp 203-204° C.

1-(5-Chloro-6-phenyl-3-pyridyl)-piperazine fumaric acid salt (Compound 1I2)

Was prepared according to method I from 1-(6-bromo-5-chloro-3-pyridyl)-piperazine. Mp 181.6-185.4° C.

Method J 1-(5-chloro-6-methyl-3-pyridyl)-4-tert-butoxycarbonyl-piperazine (Compound 1J1)

A mixture of 1-(6-bromo-5-chloro-3-pyridyl)-4-tert-butoxycarbonyl-piperazine (2.0 g, 5.3 mmol), tetramethyltin (1.9 g, 10.6 mmol), palladium-di-(triphenylphosphine (0.19 g, 0.26 mmol) and dimethylformamide (2 ml) was stirred at 160° C. in a sealed vessel overnight. The mixture was stirred in conc. hydrochloric acid (30 ml) at reflux for 15 min. The mixture was evaporated. Aqueous sodium hydroxide (50 ml, 1 M) was added and the mixture was extracted with dichloromethane (3×50 ml). Chromatography of this crude mixture on silica gel with dichloromethane, methanol and conc. ammonia (89:10:1) gave the title compound. Yield 0.70 g (43%). The corresponding salt was obtained by addition of a diethyl ether and methanol mixture (9:1) saturated with fumaric acid. Mp 178.1-180.5° C.

Method K 1-(5-Etynyl-3-pyridyl)-piperazine Fumaric Acid Salt (Compound 1K1)

A mixture of 1-(5-bromo-3-pyridyl)-4-tert-butoxycarbonyl-piperazine (53.5 g, 0.156 mol), potassium carbonate (54.0 g, 0.391 mol), copper (I) iodide (5.96 g, 31.3 mmol), palladium on carbon (20.0 g, 5%, 50% water), triphenylphosphine (4.1 g, 15.6 mmol), 2-methyl-3-butyn-2-ol (131.5 g, 1.56 mol) and dioxane (300 ml) was stirred at reflux for 10 days. The crude mixture was filtered through celite. Chromatography of this crude mixture on silica gel with ethyl acetate:petroleum (1:3) gave the corresponding alcohol. The intermediate (27.4 g, 79.3 mmol), sodium hydride (0.57 g, 23.8 mmol) and toluene (200 ml) was stirred at reflux 2 days. Chromatography of this crude mixture on silica gel with ethyl acetate:petroleum (1:3) gave the corresponding 1-(5-etynyl-3-pyridyl)-4-tert-butoxycarbonyl-piperazine. Yield 16.6 g, 73%. The protecting group was removed by stirring 1-(5-etynyl-3-pyridyl)-4-tert-butoxycarbonyl-piperazine (1.02 g, 3.55 mmol), trifluoroacetic acid (2.7 ml, 35.5 mmol) and dichloromethane (10 ml) overnight. The mixture was evaporated. Aqueous sodium hydroxide (50 ml, 1 M) was added and the mixture was extracted with dichloromethane (3×50 ml). Chromatography of this crude mixture on silica gel with dichloromethane, methanol and conc. ammonia (89:10:1) gave the title compound. Yield 0.66 g (99%). The corresponding salt was obtained by addition of a diethyl ether and methanol mixture (9:1) saturated with fumaric acid. Mp 175.1° C.

Example 2

Preparatory Example

General

All reactions involving air sensitive reagents or intermediates were performed under nitrogen and in anhydrous solvents. Magnesium sulphate was used as drying agent in the workup-procedures and solvents were evaporated under reduced pressure.

9-Methyl-3,9-diazabicyclo-[4.2.1]-nonane was prepared according to [Michaels RJ & Zaugg HE; *J. Org. Chem.* 1960 25 637].

(±) 3-(2-Naphthalyl)-9-methyl-3,9-diazabicyclo-[4.2.1]-nonane fumaric acid salt (Compound 2A)

A mixture of 2-bromonaphtalene (5.0 g; 24.1 mmol), 9-Methyl-3,9-diazabicyclo-[4.2.1]-nonane (3.38 g; 24.1 mmol) and palladacycle (0.045 g; 0.048 mmol) [*Angew. Chem. Int. Ed. Engl.* 1995 34 1844] was stirred for two days at 150° C. Sodium hydroxide (50 ml; 1 M) was added at room temperature. The mixture was extracted with diethyl ether (2×100 ml). Chromatography on silica gel with dichloromethane, methanol and conc. ammonia (89:10:1) gave the title compound. The corresponding salt was obtained by addition of a diethyl ether and methanol mixture (9:1) saturated with fumaric acid. Yield 0.30 g; 3%. Mp. 173-174° C.

(±) 3-(2-Quinolinyl)-9-methyl-3,9-diazabicyclo-[4.2.1]-nonane Fumaric Acid Salt (Compound 2B)

A mixture of 2-chloroquinoline (5.0 g; 30.6 mmol) and 9-methyl-3,9-diazabicyclo-[4.2.1]-nonane (3.38 g; 24.1 mmol) was stirred in the absence of solvent for 4 hours at 140° C. Sodium hydroxide (50 ml; 1 M) was added at room temperature. The mixture was extracted with diethyl ether (2×100 ml). Chromatography on silica gel with dichloromethane, methanol and conc. ammonia (89:10:1) gave the title compound. The corresponding salt was obtained by addition of a diethyl ether and methanol mixture (9:1) saturated with fumaric acid. Yield 5.2 g; 44%. Mp. 173.0-174.2° C.

Method A (±) 3-(3,4-Dichlorophenyl)-9-methyl-3,9-diazabicyclo-[4.2.1]-nonane Fumaric Acid Salt (Compound 2A1)

A mixture of 1-bromo-3,4-dichlorobenzene (6.65 g; 29.6 mmol) and 9-Methyl-3,9-diazabicyclo-[4.2.1]-nonane (5.0 g; 35.5 mmol), potassium-tert-butoxide (6.64 g; 59.2 mmol), tetrakis triphenylphosphine palladium(0) (1.0 g; 0.88 mmol) and 1,2-dimethoxyethane was stirred overnight. Sodium hydroxide (50 ml; 1 M) was added at room temperature. The mixture was extracted with ethyl acetate (2×40 ml). Chromatography on silica gel with dichloromethane, methanol and conc. ammonia (89:10:1) gave the title compound, Yield 2.41 g; 29%. The corresponding salt was obtained by addition of a diethyl ether and methanol mixture (9:1) saturated with fumaric acid. Mp. 114.4° C.

(±) 3-(6-Quinolinyl)-9-methyl-3,9-diazabicyclo-[4.2.1]-nonane Fumaric Acid Salt (Compound 2A2)

Was prepared according to method A, using 6-chloroquinoline as starting material and palladacycle [*Angew. Chem. Int. Ed. Engl.* 1995 34 1844], palladium acetate and 2-biphenyl-di-tert-butylphosphine as catalyst. Mp. 164-166° C.

(±) 3-(4-Fluorophenyl)-9-methyl-3,9-diazabicyclo-[4.2.1]-nonane Fumaric Acid Salt (Compound 2A3)

Was prepared according to method A. This product was separated from a reaction-mixture of 3-(3-fluorophenyl)-9-methyl-3,9-diazabicyclo-[4.2.1]-nonane and 3-(4-fluorophenyl)-9-methyl-3,9-diazabicyclo-[4.2.1]-nonane. Mp 123.7° C.

(±) 3-(3-Fluorophenyl)-9-methyl-3,9-diazabicyclo-[4.2.1]-nonane Fumaric Acid Salt (Compound 2A4)

Was prepared according to method A. This product was separated from a reaction-mixture of 3-(3-fluorophenyl)-9-methyl-3,9-diazabicyclo-[4.2.1]-nonane and 3-(4-fluorophenyl)-9-methyl-3,9-diazabicyclo-[4.2.1]-nonane. Mp 138.6° C.

(±) 3-(4-Trifluoromethoxyphenyl)-9-methyl-3,9-diazabicyclo-[4.2.1]-nonane (Compound 2A5)

Was prepared according to method A. This product was separated from a reaction-mixture of 3-(3-trifluoromethoxyphenyl)-9-methyl-3,9-diazabicyclo-[4.2.1]-nonane and 3-(4-trifluoromethoxy-phenyl)-9-methyl-3,9-diazabicyclo-[4.2.1]-nonane The product was isolated as an oil.

(±) 3-(3-Trifluoromethoxyphenyl)-9-methyl-3,9-diazabicyclo-[4.2.1]-nonane (Compound 2A6)

Was prepared according to method A. This product was separated from a reaction-mixture of 3-(3-trifluoromethoxyphenyl)-9-methyl-3,9-diazabicyclo-[4.2.1]-nonane and 3-(4-trifluoromethoxyphenyl)-9-methyl-3,9-diazabicyclo-[4.2.1]-nonane. The end product was isolated as an oil.

(±) 3-(Phenyl)-9-methyl-3,9-diazabicyclo-[4.2.1]-nonane Fumaric Acid Salt (Compound 2A7)

Was prepared according to method A. Mp 143.9° C.

Method B (±) 3-(3,4-Dichlorophenyl)-9-H-3,9-diazabicyclo-[4.2.1]-nonane Fumaric Acid Salt (Compound 2B1)

A mixture of 3-(3,4-Dichlorophenyl)-9-methyl-3,9-diazabicyclo-[4.2.1]-nonane (0.50 g; 1.8 mmol), 1-chloroethylchloroformate (0.63 g; 4.4 mmol) and xylene (10 ml) was stirred at reflux for 24 h, methanol (10 ml) was added and the mixture was stirred at reflux for 5 hours. Sodium hydroxide (50 ml; 1 M) was added at room temperature. The mixture was extracted with ethyl acetate (2×40 ml). Chromatography on silica gel with dichloromethane, methanol and conc. ammonia (89:10:1) gave the title compound. Yield 0.14 g; 29%. The corresponding salt was obtained by addition of a diethyl ether and methanol mixture (9:1) saturated with fumaric acid. Mp. 222.3° C.

3-[(5-Chloropyrid-3-yl)-5-oxyethoxyprid-3-yl]-9-Methyl-3,9-diazabicyclo-[4.2.1]-non (Compound 2B2), and O,O'-bis-[5-(9-Methyl-3,9-diazabicyclo-[4.2.1]-nonan-3-yl]-3-pyridyl]-ethyleneglycol Fumaric Acid Salt (Compound 2B3).

A mixture of O,O'-bis-(5-chloro-3-pyridyl)-ethyleneglycol (2.0 g; 7.0 mmol), 9-Methyl-3,9-diazabicyclo-[4.2.1]-nonane (3.9 g; 28.1 mmol), caesium carbonate (4.6 g; 14.0 mmol), palladacycle (0.050 g; 0.053 mmol), palladium acetate (0.050 g; 0.22 mmol), 2-biphenyl-di-tert-butyl-phosphine (0.05 g; 0.17 mmol) and tri-tert-butylphoshine (0.05 g; 0.25 mmol) was stirred at 130° C. overnight. Aqueous sodium hydroxide (50 ml; 1 M) was added and the mixture was extracted five times with diethylether (5×30 ml). The crude mixture was evaporated and purified by chromatography on silica gel with dichloromethane, methanol and conc. ammonia (89:10:1) gave the title compound (A) as free base. Yield 0.40 g; 20%. Mp. 112-113° C., and (B) yield 0.40 g; 15%. The corresponding salt of B was obtained by addition of a diethyl ether and methanol mixture (9:1) saturated with fumaric acid. Mp. 84-88° C.

O,O'-bis-(5-chloro-3-pyridyl)-ethyleneglycol

A mixture of ethyleneglycol (138.4 g; 2.23 mol) and sodium (12.3 g; 0.53 mol) was stirred at 80° C. for 4 hours. 3,5-Dichloropyridine (66.0 g; 0.45 mol) and dimethyl sulfoxide (300 ml) was stirred at 110° C. for 10 hours. The mixture was allowed to reach room temperature. Aqueous sodium hydroxide (1 M; 600 ml) was added, the mixture was stirred and filtered. The title compound was isolated as a crystalline product was isolated (8.7 g; 6.8%). Mp. 136-138° C.

Example 3

Biological Activity

Mouse Forced Swim Test

Systemic administration of a classical antidepressant (Desipramine) induces an increase in the forced swim distance performed by mice in a small water pool. The Forced Swim Test therefore is considered predictive of a potential antidepressant pharmacological effect.

Female NMRI mice (of 20-25 g) are habituated to the laboratory (a 12 hour light/dark cycle) for at least 16 hours before the experiment.

30 minutes after s.c. injection of either vehicle or drug, the mouse is placed in a glass beaker (d=16 cm; 5000 ml) with water (24° C.) up till 10 cm from the top edge. For the subsequent 6 minutes the duration of immobility defined as swim speed less than 2.5 cm/minute, and forced swim distance defined as distance swum with a speed above 5 cm/minute, is recorded. There are 8 mice in each group.

The activity of the mouse is tracked by the View Point system for the measurement of distance, immobility, and speed.

Time of immobility ±SEM (seconds) and forced swim distance ±SEM (cm) in 15 seconds time intervals are presented and plotted in SigmaPlot. Mean total immobility time and total swim distance in the time interval 60-360 seconds are calculated and presented for each group. The dose showing significant difference from the vehicle treated group is reported as the Minimal Effective Dose (MED s.c. mg/kg).

1-(6-Chloro-3-pyridyl)-piperazine (Compound 1C3 of Example 1) (0.3, 1, 3, 10 mg/kg s.c.) was tested in the mouse Forced Swim Test (mFST) and it did not affect forced swimming with a 30 minutes pre-treatment. However, the combination of Venlafaxine and Compound 1C3 (1+3; 3+3; 10+1; 10+3 mg/kg s.c.) significantly increased the forced swimming in NMRI mice.

Similar effect has been observed with the combination of Venlafaxine (10 mg/kg s.c.) and the homopiperazine 1-(6-chloro-3-pyridyl)-homopiperazine (0.1, 0.3 mg/kg s.c.) that is disclosed in WO 99/21834 as Compound 9K; and Venlafaxine (10 mg/kg s.c.) and the homopiperazine 1-(5-ethynyl-3-pyridyl)-homopiperazine (0.1, 0.3 mg/kg s.c.) that is disclosed in WO 99/21834 as Compound 12J; and Venlafaxine (10 mg/kg s.c.) and the homopiperazine 1-(3-pyridyl)-homopiperazine (0.1, 0.3 mg/kg s.c.) that is disclosed in WO 99/21834 as Compound 1F.

The invention claim is:

1. An 8-azabicyclo[3.2.1]oct-2-ene compound of Formula VI,

(VI)

any of its enantiomers or any mixture of its enantiomers, or a pharmaceutically acceptable salt thereof; wherein R is hydrogen; and $R^1$ is benzothienyl.

2. The 8-azabicyclo[3.2.1]oct-2-ene compound of claim 1, which is (±)-3-(2-benzothienyl)-8-H-8-azabicyclo[3.2.1]oct-2-ene;

or an enantiomer or a mixture of its enantiomers, or a pharmaceutically acceptable salt thereof.

3. A pharmaceutical composition comprising a therapeutically effective amount of the 8-azabicyclol[3.2.1]oct-2-ene compound of claim 1, together with at least one pharmaceutically acceptable carrier or diluent.

4. A method of treatment of an affective disorder, disease, or condition in a subject, which method comprises administering to said subject a therapeutically effective amount of the 8-azabicyclo[3.2.1]oct-2-ene compound of claim 1.

5. The method of claim 4, wherein the affective disorder, disease, or condition is depression, anxiety, obsessive compulsive disorder (OCD), or panic disorder.

6. The method of claim 4, wherein the affective disorder, disease, or condition is pain.

7. The 8-azabicyclo[3.2.1]oct-2-ene compound of claim 1, wherein R is 2-benzothienyl $R^1$ or 3-benzothienyl.

* * * * *

UNITED STATES PATENT AND TRADEMARK OFFICE
CERTIFICATE OF CORRECTION

| | | |
|---|---|---|
| PATENT NO. | : 7,307,087 B2 | Page 1 of 1 |
| APPLICATION NO. | : 10/380653 | |
| DATED | : December 11, 2007 | |
| INVENTOR(S) | : Gunnar Olsen et al. | |

It is certified that error appears in the above-identified patent and that said Letters Patent is hereby corrected as shown below:

In column 20, lines 64-65 should read as follows:

7. The 8-azabicyclo[3.2.1]oct-2-ene compound of claim 1, wherein $R^1$ is 2-benzothienyl or 3-benzothienyl.

Signed and Sealed this

Twenty-ninth Day of April, 2008

JON W. DUDAS
*Director of the United States Patent and Trademark Office*

UNITED STATES PATENT AND TRADEMARK OFFICE
CERTIFICATE OF CORRECTION

PATENT NO.        : 7,307,087 B2                                           Page 1 of 1
APPLICATION NO.   : 10/380653
DATED             : December 11, 2007
INVENTOR(S)       : Gunnar Olsen et al.

It is certified that error appears in the above-identified patent and that said Letters Patent is hereby corrected as shown below:

On the Title Page, in the left column, item (60) is inserted before item (30), as follows:

Related U.S. Application Data

(60)  Provisional application No. 60/242,146, filed on Oct. 23, 2000.

Signed and Sealed this

Eighth Day of July, 2008

JON W. DUDAS
*Director of the United States Patent and Trademark Office*